United States Patent [19]
Desai et al.

[11] Patent Number: 5,677,436
[45] Date of Patent: Oct. 14, 1997

[54] PROCESS FOR MAKING ALKYL POLYGLOSIDES HAVING IMPROVED AESTHETIC AND TACTILE PROPERTIES

[75] Inventors: Sureshchandra G. Desai, Wayne; John Frederick Hessel, Metuchen, both of N.J.; Allen D. Urfer, Shelbyville, Ind.; Charles B. Allen, Norristown, Pa.

[73] Assignee: Henkel Corporation, Plymouth Meeting, Pa.

[21] Appl. No.: 641,170

[22] Filed: Apr. 30, 1996

Related U.S. Application Data

[62] Division of Ser. No. 338,701, Nov. 10, 1994, Pat. No. 5,567,808.
[51] Int. Cl.$^6$ ............................. C07H 15/00; C07H 17/00
[52] U.S. Cl. ............................................. 536/4.1; 536/18.1
[58] Field of Search .................................... 536/4.1, 18.1

[56] References Cited

U.S. PATENT DOCUMENTS

| | | | |
|---|---|---|---|
| 4,396,520 | 8/1983 | Payne et al. | 252/89.1 |
| 4,483,787 | 11/1984 | Jones et al. | 252/551 |
| 4,536,317 | 8/1985 | Llenado et al. | 252/174.17 |
| 4,536,318 | 8/1985 | Cook et al. | 252/174.17 |
| 4,599,188 | 7/1986 | Llenado | 252/174 |

*Primary Examiner*—Nathan M. Nutter
*Attorney, Agent, or Firm*—Wayne C. Jaeschke; John E. Drach; Steven J. Trzaska

[57] ABSTRACT

A composition and process for enhancing the aesthetic and tactile properties of an alkyl polyglycoside involving combining a first alkyl polyglycoside having the general formula I:

$$RO(Z)_a \qquad (I)$$

wherein R is a monovalent organic radical having from about 8 to about 18 carbon atoms; Z is a saccharide residue having 5 or 6 carbon atoms; and a is a number having a value from about 1 to about 6, with an additive selected from the group consisting of $C_6$–$C_{10}$ alkyl sulfates, unsaturated aliphatic carboxylic acids including hydroxy-substituted derivatives thereof or their salts, unsaturated aliphatic sorbitan esters, $C_8$–$C_{36}$ branched aliphatic di-carboxylic acids, $C_6$–$C_{54}$ branched aliphatic tri-carboxylic acids, alkyl sulfosuccinates, a second alkyl polyglycoside having an alkyl group with from 4 to 10 carbon atoms, alkyl alkoxylates, alkyl and aryl phosphate esters, branched aliphatic carboxylic acids, unsaturated alcohols, Guerbet alcohols, alkoxylated C 6 to C 18 alkyl polyglycosides, alkoxylated penterythritol, alkoxylated penterythritol esters, alkyl and aryl sulfonates, alkyl sulfonates, alkenyl sulfonates, alkyl amino carboxylates or imino dicarboxylates, betaines, carboxylated imidazoline derivatives, carboxylate surfactants, and mixtures thereof.

29 Claims, 8 Drawing Sheets

PROCESS FOR MAKING ALKYL POLYGLOSIDES HAVING IMPROVED AESTHETIC AND TACTILE PROPERTIES

CONTINUING DATA

This application is a Divisional of application Ser. No. 08/338,701, filed Nov. 10, 1994, and now U.S. Pat. No. 5,567,808.

FIELD OF THE INVENTION

The present invention relates to a composition and process for enhancing the tactile and aesthetic properties of alkyl polyglycosides. More particularly, by adding an effective amount of an additive to an alkyl polyglycoside, both the tactile and aesthetic properties of alkyl polyglycosides are significantly enhanced.

BACKGROUND OF THE INVENTION

The aesthetic properties of alkyl polyglycoside solutions are apt to erode over a short period of time due to the crystallization of the alkyl polyglycoside. Once the alkyl polyglycoside solutions crystallize, the viscosity of the solutions increases to the point where handling problems result due to the non-homogeneity of the product. The crystallization phenomenon in fats and lipids is well known. All fats and lipids commonly form lamella-type structures, but every substance reveals different unit cell structures, i.e., polymorphism. The crystal structure of each modification depends on the geometrical conformation and chemical bonding of a molecule in which molecular interactions differ between different segments, such as an aliphatic chain, an olefin group in unsaturated fatty species, a methyl end group which stabilizes the lamella-lamella interface, a glycerol group in acylglycerol, —COOH in fatty acid, a polar head group in polar lipids, etc. Strongly hydrated nonionic surfactants have phase diagrams resembling those of ionic surfactants, suggesting the presence of a strong repulsive force between the micelles. These strong hydration repulsion forces are oftentimes balanced by van der Waals attractive forces between the lipid bilayers which provide for a uniform mixture.

It is well known that at a temperature below the critical transition temperature, a surfactant-water mixture exists in the so-called coagel and gel states, where the hydrocarbon chains of surfactant molecules are in a trans zigzag elongated state. A difference between the coagel and gel phases can be clearly recognized by the naked eye. That is, the gel phase is in a homogeneous, semi-transparent state, while the coagel phases consist of a hydrated-crystalline state separated from the water solution phase. This is considered to be due to the difference in the mode of binding forces operating in the polar head region in the two phases. Probably, the predominant binding force in the coagel phase is electrostatic interaction between cationic head groups and their counter-ions, while there are in the gel phase hydration interactions of both with water molecules.

Physical deterioration of fat products such as margarine, shortening, and chocolate, just to name a few, depends on the size, morphology and polymorphic structure of the fat crystals, all of which are primarily influenced by the crystallization conditions, and secondly, by the phase transformation.

Kinetic parameters in the crystallization processes involve molecular clustering, solvation/desolvation, adsorption, surface/volume diffusion, conformational rearrangements and so on.

Crystallization involves two elementary processes: nucleation and crystal growth. Nucleation occurs when the solution or melt phases deviate from thermodynamic equilibria to a greater extent. Three actual nucleation phenomena occur in real systems. They are homogeneous nucleation which occurs in a very pure system and at a higher driving force. Heterogeneous nucleation predominates either in an impure system or at a lower driving force. Secondary nucleation which becomes important when the pre-existing crystals provide secondary nuclei so that the precipitation is remarkably enhanced.

Certain alkyl polyglycosides have a tendency to crystallize during storage at ambient temperatures due to their supersaturated state. Upon crystallization, the alkyl polyglycosides become turbid, i.e., cloudy and opaque in appearance due to the solids contained therein falling out of their supersaturated state which, when coupled with the resultant non-homogeneous state of the crystallized solution and the attendant difficulties in handling operations such as pumping, is a highly undesirable phenomenon. In order to rectify this undesirable physical state, the alkyl polyglycoside composition must be heated in order to resolvate the crystals. As can be imagined, this process is both expensive and time-consuming.

Another problem associated with alkyl polyglycosides relates to the undesirable tactile properties which they impart upon contact with the human body, commonly referred to in the industry as "scroopiness". More particularly, alkyl polyglycosides, when applied onto hair and/or skin tend to make it feel rough, dry and sticky as if hairspray were applied thereon. In general, alkyl polyglycosides, due to their nonionic character, synergistic relationship with other surfactants, tendency towards high foaming and mildness with respect to skin irritation, have become highly desirable surfactants for use in the personal care products industry. However, due to their tendency to impart this highly undesirable scroopiness effect when in contact with the human body, their use in the personal care industry, in significant amounts, has been limited.

Typical commonly used hydrotropes such as ethanol and SXS have proven to be ineffective for maintaining the homogeneity of alkyl polyglycoside solutions, and thus inhibiting crystallization.

Consequently, it is the primary object of this invention to provide a composition and process of enhancing the aesthetic properties of alkyl polyglycosides by either reducing or eliminating their tendency to crystallize during prolonged storage under ambient conditions.

It is also an object of this invention to eliminate scroopiness in human hair and/or skin as a result of treatment with cleansing compositions containing alkyl polyglycosides.

SUMMARY OF THE INVENTION

Other than in the operating examples, or where otherwise indicated, all numbers expressing quantities of ingredients or reaction conditions used herein are to be understood as modified in all instances by the term "about".

Briefly stated, the present invention is directed to a composition comprising a first alkyl polyglycoside having the general formula I $$RO(Z)_a \qquad (I)$$

wherein R is a monovalent organic radical having from about 12 to about 16 carbon atoms; Z is a saccharide residue having 5 or 6 carbon atoms; and a is a number having a value from about 1 to about 6 and an additive selected from the group consisting of $C_6$–$C_{10}$ alkyl sulfates, unsaturated aliphatic carboxylic acids including their hydroxy-substituted derivatives or their salts, unsaturated aliphatic sorbitan esters, $C_8$–$C_{36}$ branched aliphatic di-carboxylic acids, $C_6$–$C_{54}$ branched aliphatic tri-carboxylic acids, alkyl sulfosuccinates, a second alkyl polyglycoside wherein the alkyl group has from 4 to 10 carbon atoms, alkyl alkoxylates, alkyl and aryl phosphate esters, branched aliphatic carboxylic acids, unsaturated alcohols, Guerbet alcohols, alkoxylated C6 to C18 aliphatic polyglycosides, alkoxylated penterythritol, alkoxylated penterythritol esters, alkyl and aryl sulfonates, alkyl sulfonates, alkenyl sulfonates, alkyl amino carboxylates or imino dicarboxylates, betaines, carboxylated immidazoline derivatives, carboxylate surfactants, and mixtures thereof, in a weight ratio of first alkyl polyglycoside to additive of from about 500:1 to about 15:1, respectively.

The present invention also provides a process for enhancing the aesthetic and tactile properties of alkyl polyglycosides comprising adding an effective amount of an additive selected from the group consisting of $C_6$–$C_{10}$ alkyl sulfates, unsaturated aliphatic carboxylic acids including hydroxy-substituted derivatives thereof or their salts, unsaturated aliphatic sorbitan esters, $C_8$–$C_{36}$ branched aliphatic di-carboxylic acids, $C_6$–$C_{54}$ branched aliphatic tri-carboxylic acids, alkyl sulfosuccinates, a second alkyl polyglycoside wherein the alkyl group has from 4 to 10 carbon atoms, alkyl alkoxylates, alkyl and aryl phosphate esters, branched aliphatic carboxylic acids, unsaturated alcohols, Guerbet alcohols, alkoxylated C 6 to C 18 alkyl polyglycosides, alkoxylated penterythritol, alkoxylated penterythritol esters, alkyl and aryl sulfonates, alkyl sulfonates, alkenyl sulfonates, alkyl amino carboxylates or imino dicarboxylates, betaines, carboxylated immidazoline derivatives, carboxylates, and mixtures thereof, to a first alkyl polyglycoside of the formula I $$RO(Z)_a \qquad (I)$$

wherein R is a monovalent organic radical having from about 12 to about 16 carbon atoms; Z is a saccharide residue having 5 or 6 carbon atoms; and a is a number having a value from about 1 to about 6.

The present invention also provides a process for enhancing the tactile properties of alkyl polyglycoside solutions when applied onto human hair and/or skin by contacting human hair and/or skin with a composition comprised of:

(a) an alkyl polyglycoside of formula I:

$$RO(Z)_a \qquad I$$

wherein R is a monovalent organic radical having from about 8 to about 18 carbon atoms; Z is a saccharide residue having 5 or 6 carbon atoms; a is a number having a value from 1 to about 6 and an effective amount of a dicarboxylic acid having from 8 to about 36 carbon atoms;

(b) a salt of an alkyl ether sulfate having an average degree of ethoxylation of about 2; and (c) an N-alkoxylated fatty acid amide, thereby imparting to said human hair, skin and combinations thereof a feeling which is free of tackiness, roughness, dryness and combinations thereof.

DETAILED DESCRIPTION OF THE INVENTION

Figure 1:
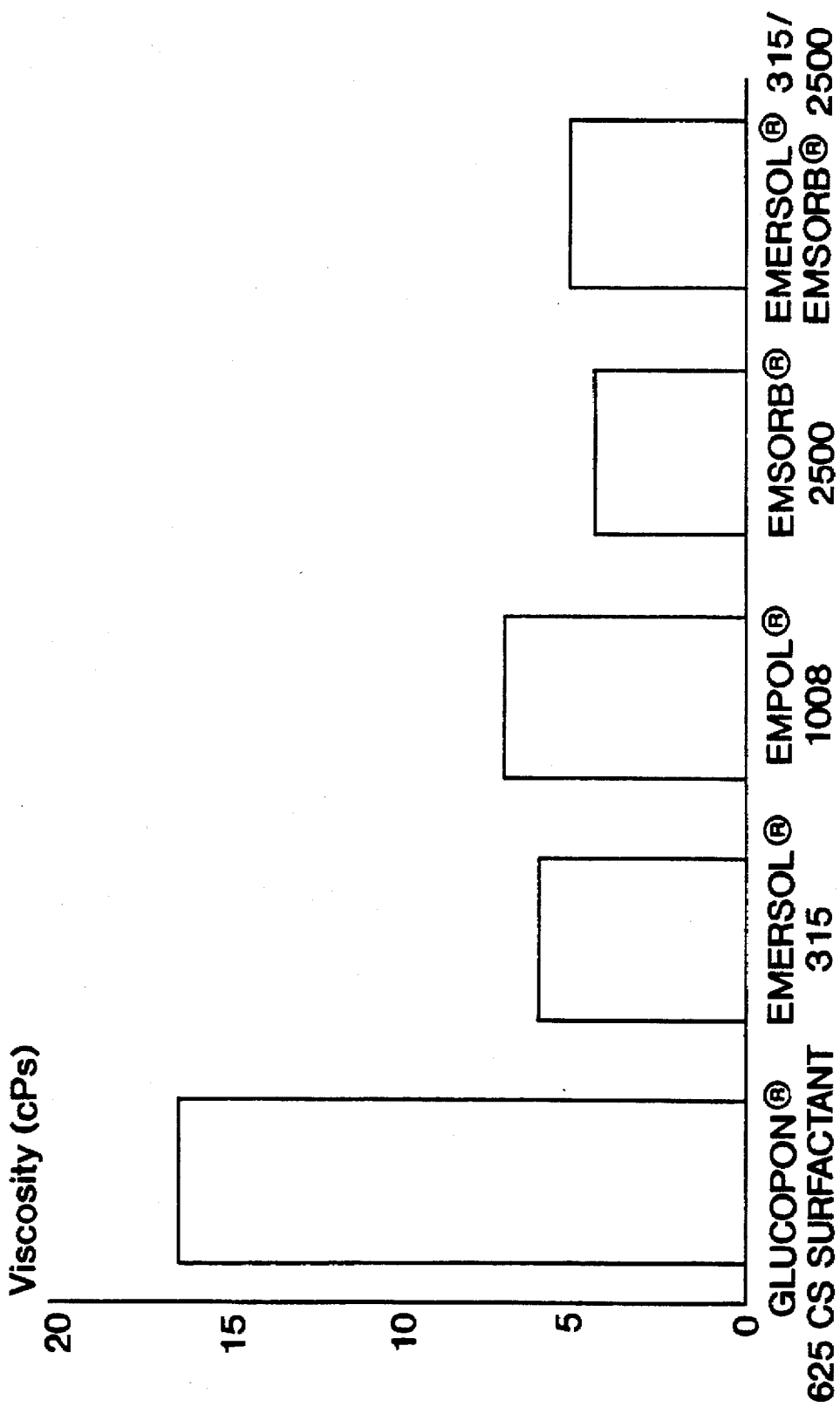
FIG. 1 is a bar graph illustrating the effect on viscosity at a temperature of about 72° F., when various unsaturated fatty acids such as EMERSOL® 315, an unsaturated carboxylic acid, EMPOL® 1008, an unsaturated aliphatic dicarboxylic acid, and EMSORB® 2500, an unsaturated alkyl sorbitan ester, are added at a 1.5% actives level to GLUCOPON® 625 CS SURFACTANT at about 40% actives.

In general, it is desirable to improve both the aesthetic and tactile properties of alkyl polyglycosides.

An alkyl polyglycoside is a sugar derivative surfactant which is typically less irritating to human skin than other surfactants. Also, though it is a nonionic surfactant, an alkyl polyglycoside forms a stable foam per se, and furthermore, exerts a foam-stabilizing effect when combined with anionic surfactants. Conventional body cleansers such as shampoos, whether for hair or body, contain anionic surfactants as their major components. Because of the low skin irritation associated with the use of alkyl polyglycosides as the nonionic surfactant, the use of alkyl polyglycosides as an ingredient has become an option in the personal care industry. However, prior to their admixture into cleaning compositions, there is a time period during which the alkyl polyglycosides are shipped from the manufacturer and stored in drums. It is during this time period, which may be very short, and under ambient conditions, the alkyl polyglycosides have a tendency to crystallize, thus becoming turbid and more viscous. Moreover, as was mentioned above, the use of alkyl polyglycosides as hair and/or skin cleansers, until now, has been limited because of the previously-described undesirable scroopiness effect imparted by alkyl polyglycosides when in contact with the human body. Thus, these alkyl polyglycosides are used primarily in small quantities for their synergistic relationship with other surfactants, low skin irritation and tendency to high foaming.

It has now surprisingly been found that by adding an effective amount of the disclosed additives to alkyl polyglycosides, alkyl polyglycosides may be used as the primary surfactant in a personal care product formulation, while at the same time exhibiting significantly enhanced aesthetic properties based on the elimination or reduction in crystallization, along with the resultant increase in viscosity of the alkyl polyglycosides.

Thus, according to the present invention, there is provided a composition having improved aesthetic and tactile properties comprising a mixture of a first alkyl polyglycoside of formula I $$RO(Z)_a \tag{I}$$

wherein R is a monovalent organic radical having from about 8 to about 18 carbon atoms; Z is a saccharide residue having 5 or 6 carbon atoms; and a is a number having a value from about 1 to about 6, and an additive selected from the group consisting of $C_6$–$C_{10}$ alkyl sulfates, unsaturated aliphatic carboxylic acids including hydroxy-substituted derivatives thereof or their salts, unsaturated aliphatic sorbitan esters, $C_8$–$C_{36}$ branched aliphatic di-carboxylic acids, $C_6$–$C_{54}$ branched aliphatic tri-carboxylic acids, alkyl sulfosuccinates, a second alkyl polyglycoside wherein the alkyl group has from 4 to 10 carbon atoms, alkyl alkoxylates, alkyl and aryl phosphate esters, branched aliphatic carboxylic acids, unsaturated alcohols, Guerbet alcohols, alkoxylated C 6 to C 18 alkyl polyglycosides, alkoxylated penterythritol, alkoxylated penterythritol esters, alkyl and aryl sulfonates, alkyl sulfonates, alkenyl sulfonates, alkyl amino carboxylates, or imino dicarboxylates, betaines, carboxylated immidazoline derivatives, carboxylate surfactants, and mixtures thereof.

In the aspect of the present invention which relates to the elimination of the crystallization of alkyl polyglycosides, the preferred alkyl polyglycosides are those which are most susceptible to crystallization upon storage. Such alkyl polyglycosides are alkyl polyglucosides wherein the alkyl groups contain from 12 to 16 carbon atoms and the sugar residue is derived from glucose. Such alkyl polyglucosides which are made by reacting a mixture of fatty alcohols having 12 to 16 carbon atoms and glucose and are available commercially, for example, from Henkel Corporation as GLUCOPON® 600 and GLUCOPON® 625 SURFACTANT, or APG® 600 and APG 625 SURFACTANT.

These alkyl polyglycosides have an average degree of polymerization, which is typically defined as the average number of repeat units, or in this case glucose units, per polymer chain, in the range of about 1.4 to about 1.6. The pH of the alkyl polyglycoside is typically in the range of about 6 to about 12. The percent actives of the alkyl polyglycosides employed in the present invention is in the range of about 5 to about 80%, and preferably about 40%.

The $C_6$–$C_{10}$ alkyl sulfates which may be employed are short-chain alkyl sulfates characterized by the formula $R'$—$SO_4^-$—$X^+$ wherein X is Na, K, Mg, and $NH_3$. These can be manufactured from alkyl alcohols by sulfation with $SO_3$ or chlorosulfonic acid.

The unsaturated aliphatic carboxylic acids, including their hydroxy-substituted derivatives and salts thereof, employed in the present invention have from 6 to 22 carbon atoms.

Preferred unsaturated fatty acids include: linoleic acid and its sodium or potassium salt (commercially available under the tradename EMERSOL® 315); linseed fatty acid (commercially available under the tradename EMERY® 643); or hydroxy-substituted unsaturated aliphatic carboxylic acids such as ricinoleic acid, and mixtures thereof.

Unsaturated aliphatic sorbitan esters of the type

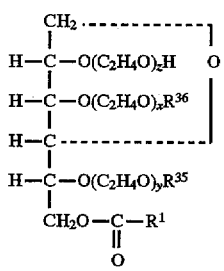

wherein each of $R^{35}$ and $R^{36}$ is independently hydrogen or $OCR^1$ and wherein $R^1$ is a $C_{10-22}$ hydrocarbon radical with the proviso that x+y+z is a number from 5–30, may also be used.

Dimer fatty acids and salts thereof having the structure X—$R^2$—X where $R^2$ is a $C_{8-36}$ hydrocarbon radical and X is COOH may also be employed. Examples include the potassium salt of dimer acid (commercially available under the tradename EMPOL® 1008).

Similarly, trimer fatty acids having from about 6 to about 54 carbon atoms may also be employed as an additive.

Aliphatic dicarboxylic acids of the formula $R^3$—CX—$(COOH)_2$ wherein $R^3$ is a $C_{16-18}$ hydrocarbon radical and X is $NH_2$ or $N(R^4)_2$, where $R^4$ is a $C_{1-4}$ hydrocarbon radical may also be used.

Short-chain alkyl polyglycosides wherein the alkyl group has from about 4 to about 10 carbon atoms may also be used to inhibit crystallization.

Alkyl alkoxylates having the structure $R^5$—$(EO)_v$—$(PO)_w$—OH wherein $R^5$ is a $C_{8-22}$ hydrocarbon radical, v is a number from about 0 to about 100 and w is a number from about 0 to about 100, such that v+w≧1, may also be employed.

Yet another additive which may be employed are the alkyl sulfosuccinates characterized by the structure

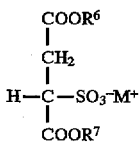

wherein each of $R^6$ and $R^7$ is independently a $C_{8-18}$ linear or branched, saturated or unsaturated hydrocarbon radical or H, with the proviso that when $R^6$ is H, $R^6$ does not equal $R^7$, and $M^+$ is Na, K or ammonium.

Alkyl and aryl phosphate esters characterized by the structure

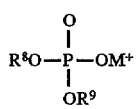

wherein each of $R^8$ and $R^9$ is independently a $C_{8-22}$ straight or branched, saturated or unsaturated hydrocarbon radical which may be ethoxylated with from 0 to 20 moles of ethylene oxide, or H, with the proviso that when $R^8$ is H, $R^8$ does not equal $R^9$, and $M^+$ is H, Na, K, or ammonium.

Branched fatty acids of the $R^{10}$—COOH type where $R^{10}$ is a $C_{4-22}$ hydrocarbon radical.

Unsaturated alcohols of the $R^{11}$—OH type may also be employed.

Guerbet alcohols having the formula

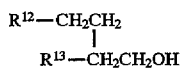

wherein each of $R^{12}$ and $R^{13}$ is independently a $C_{8-10}$ straight or branched chain hydrocarbon radical, and also esters of Guerbet alcohols of the formula $R^{14}COOR^{15}$ where

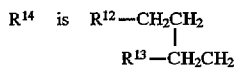

and $R^{15}$ is a $C_{8-18}$ hydrocarbon radical.

Another useful additive is an alkoxylated alkyl polyglycoside having the formula

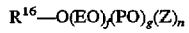

where Z is a glucose residue and n is a number from about 1 to 5, f is from about 0 to 100 and g is from about 0 to 100 where f+g≧1.

Ethoxylated penterythritol and its esters having the formula

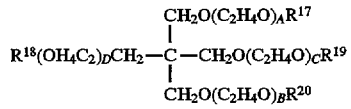

where A+B+C+D is a number from 40–200 and wherein each of $R^{17}$–$R^{20}$ is independently H or $OCR^{40}$ wherein $R^{40}$ is a $C_{6-22}$ hydrocarbon radical.

Aliphatic or alkyl and aryl sulfonates having the formula $R^{21}$—$SO_3^-M^+$ wherein $R^{21}$ is a $C_{8-22}$ straight or branched chain, saturated or unsaturated alkyl and aryl group, may also be employed.

Alkyl amino carboxylates or imino dicarboxylates having the formula $R^{22}$—$NR^{23}CH_2CH_2COO^-M^+$ wherein $R^{22}$ is a $C_{8-18}$ aliphatic radical, linear or branched, saturated or unsaturated, $R^{23}$ is H or $CH_2CH_2COO^-$ and M is Na, K or ammonium.

Betaines having the formula:

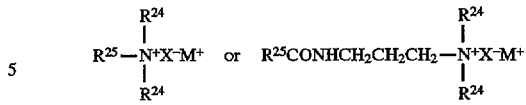

wherein $R^{25}$ is a $C_{8-22}$ straight or branched chain, saturated or unsaturated aliphatic radical, $R^{24}$ is methyl or 2-hydroxy ethyl, $X^-$ is $CH_2COO^-$ or $CH_2CH(OH)CH_2SO_3^-$, and $M^+$ is Na, K or ammonium.

Carboxylated immidazoline derivatives of the type $R^{26}CONHCH_2CH_2NR^{27}R^{28}$ wherein $R^{26}$ is a $C_{8-22}$ alkyl group, straight or branched chain, saturated or unsaturated, $R^{27}$ is $CH_2COONa$ or $CH_2CH(OH)CH_2SO_3Na$, and $R^{28}$ is $CH_2CH_2OH$ can also be employed.

Carboxylate surfactants of the formula $R^{29}$—$COOM^+$ wherein $R^{29}$ is $C_{8-22}$ alkyl group, straight or branched chain, or $R^{30}CONCH_3CH_2$ with $R^{30}$ is a $C_{8-22}$ group (i.e. sarcosinate), and $M^+$ is Na, K or ammonium.

In a preferred embodiment of the present invention the weight ratio of first alkyl polyglycoside to additive, present in the composition, is from about 500:1 to about 15:1, respectively. A particularly preferred ratio is about 25:1. The percent actives of the alkyl polyglycosides is in the range of from about 5–80%, and most preferably about 40%.

According to another aspect of the present invention, there is also provided a process for enhancing the aesthetic and tactile properties of alkyl polyglycosides involving adding an effective amount of an additive to a first alkyl polyglycoside of formula I:

$$RO(Z)_a \qquad (I)$$

wherein R is a monovalent organic radical having from about 8 to about 18 carbon atoms; Z is a saccharide residue having 5 or 6 carbon atoms; and a is a number having a value from about 1 to about 6. The additives which may be employed are the same as those described above.

In a preferred embodiment of the present invention, an alkyl polyglycoside according to formula I is heated to a temperature in the range of from about 35° to about 70° C., and preferably about 40° C. The additive is then added to the heated alkyl polyglycoside, with mixing, in a weight ratio of about 500:1 to about 15:1, and preferably about 25:1. The addition of these types of additives has been shown to be enhance the aesthetic and tactile properties of alkyl polyglycosides without adversely affecting their physical and performance properties.

The practice of this invention may be further appreciated by consideration of the following non-limiting, working examples, and the benefits of the invention may be further appreciated by reference to the comparison examples.

Crystallization Inhibition

EXAMPLES

Alkyl polyglycoside compositions listed in Table I were prepared. The crystallization inhibiting effect of each composition was evaluated according to the following method. The results are also shown in Table I.

Evaluation Method

Figure 2:
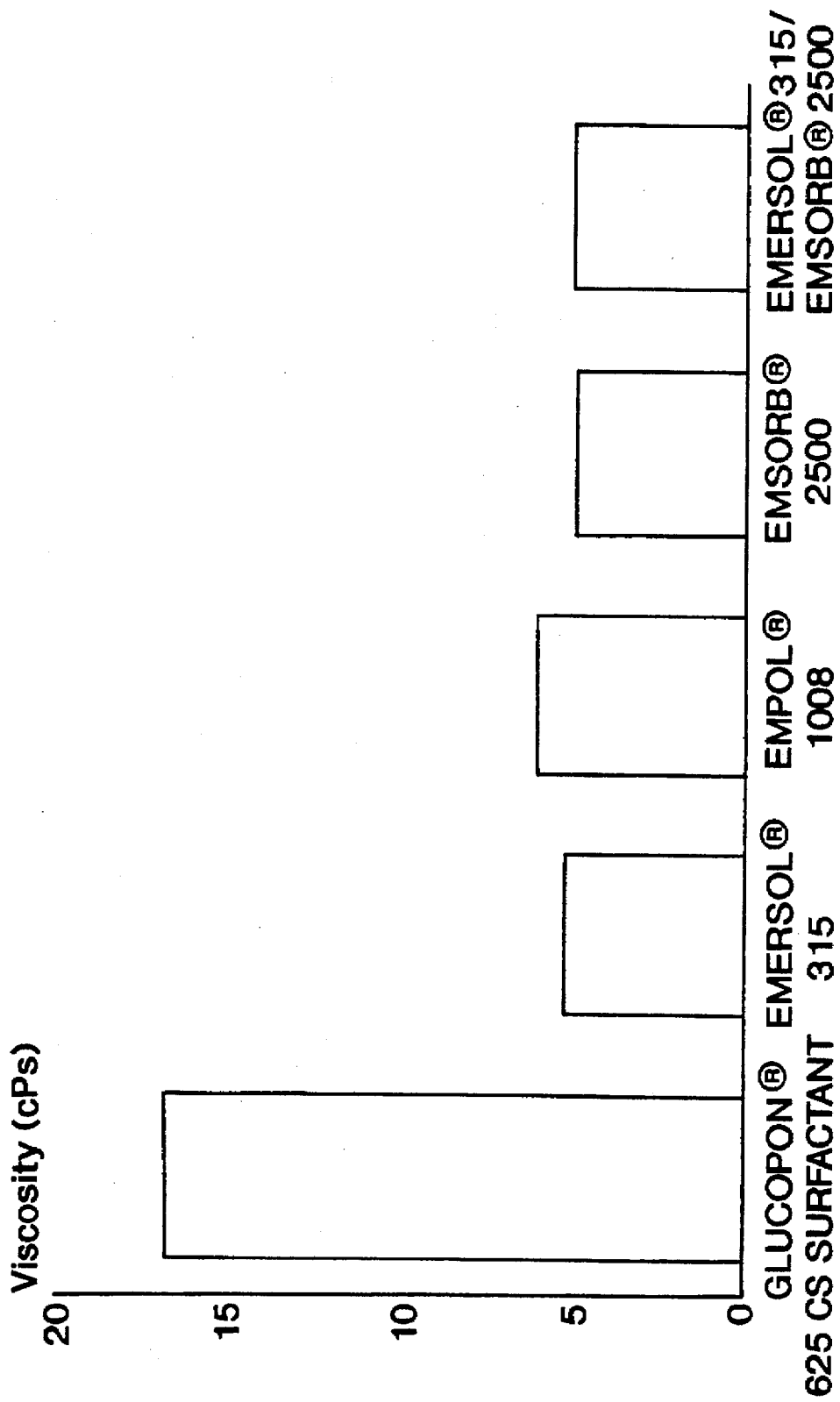
FIG. 2 is a bar graph illustrating the effect on viscosity, at a temperature of about 72° F. when the unsaturated fatty acids of FIG. 1 are added at a 1.5% actives to GLUCOPON® 625 CSUP SURFACTANT at about 40% actives.
Figure 3:
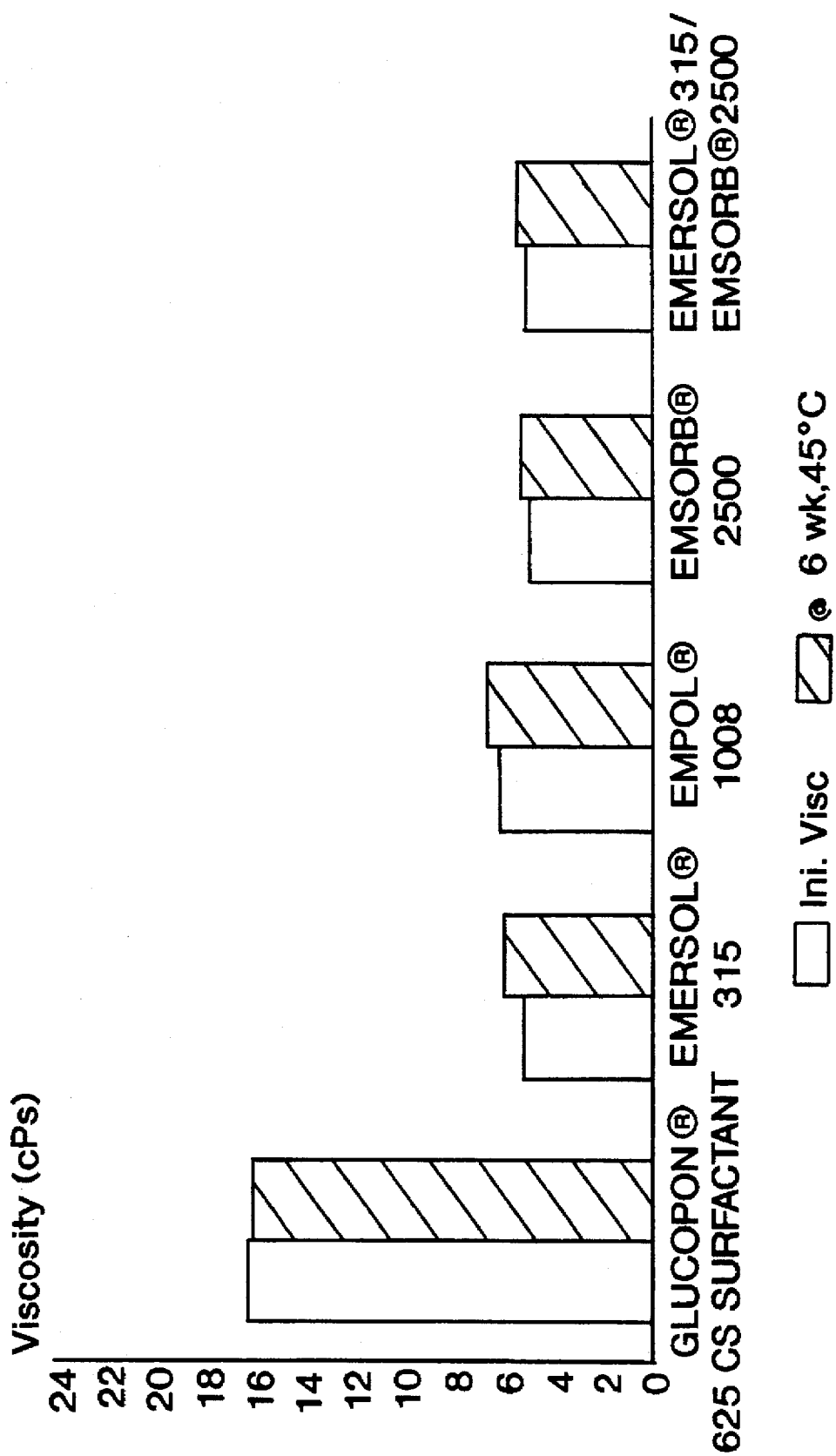
FIG. 3 is a bar graph comparing the initial viscosity at 72° F. when the unsaturated fatty acids of FIG. 1 are added at a 1.5% actives to GLUCOPON® 625 CSUP SURFACTANT at about 40% actives versus the viscosity after approximately six weeks of storage at about 45° C.
Figure 4:
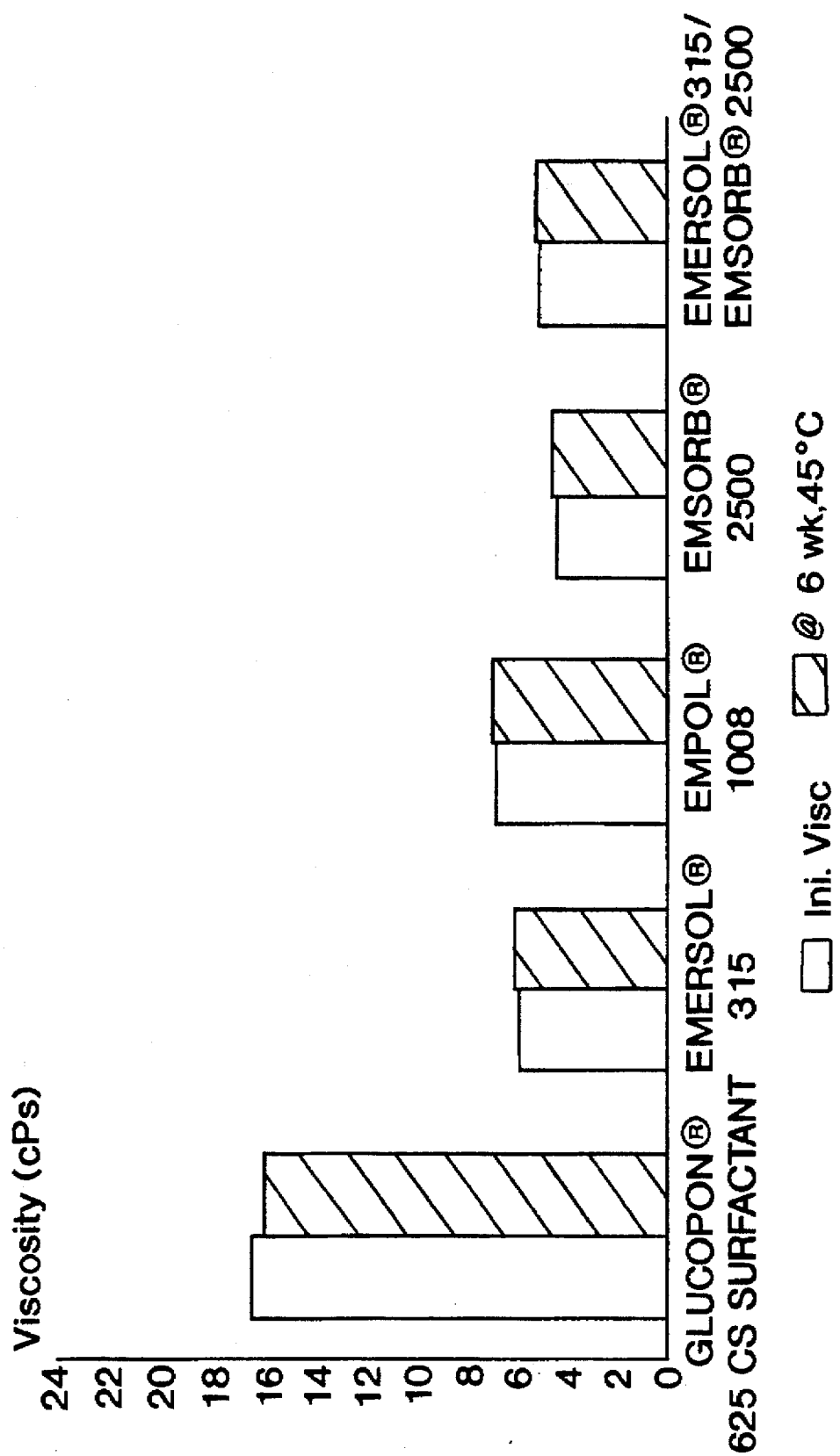
FIG. 4 is a bar graph comparing the initial viscosity at 72° F. when the unsaturated fatty acids of FIG. 1 are added at a 1.5% actives to GLUCOPON® 625 CS SURFACTANT at about 40% actives versus the viscosity after approximately six weeks of storage at about 45° C.
Figure 5:
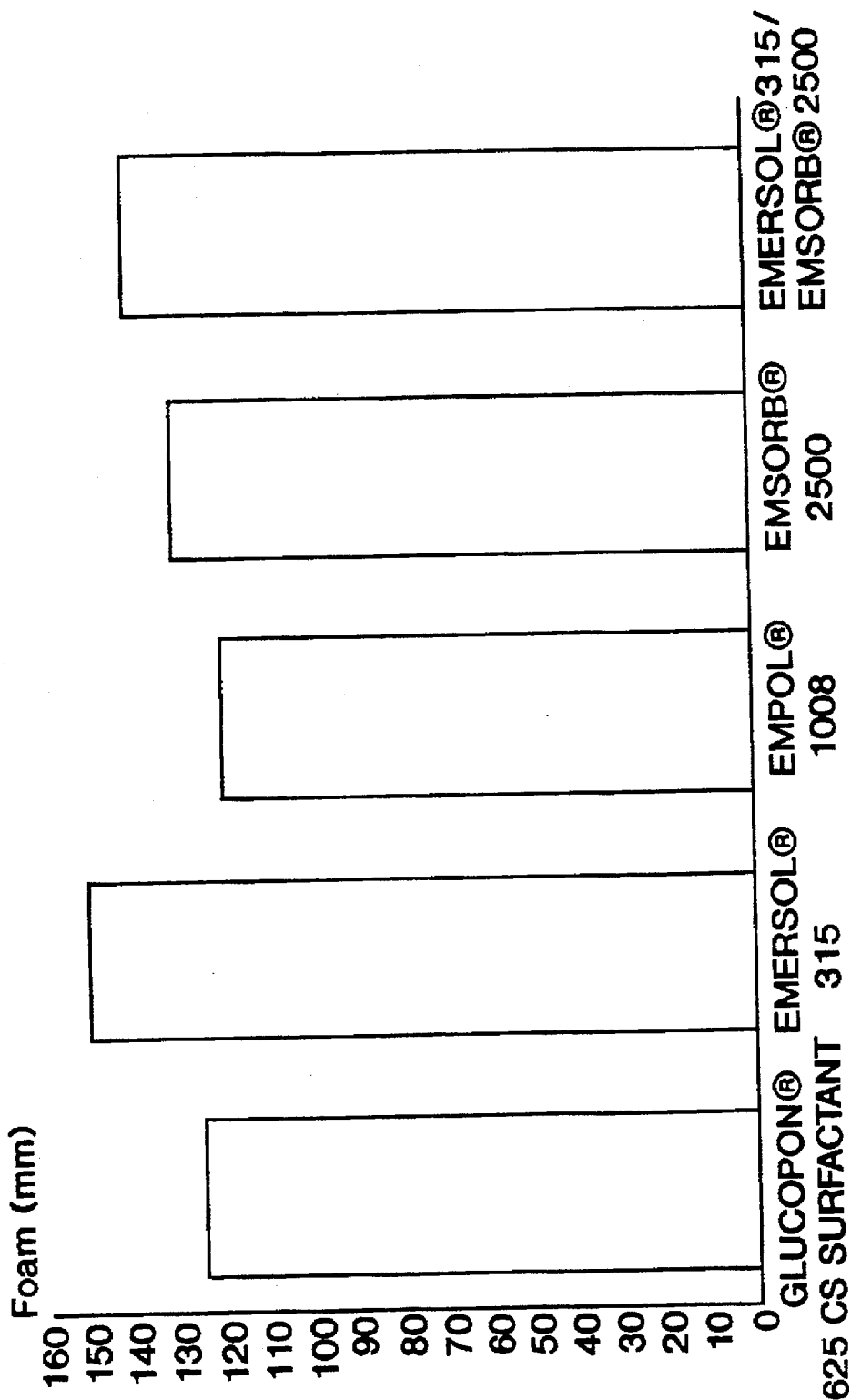
FIG. 5 is a bar graph illustrating the effect on the amount of foam formed at 72° F. in deionized water when the unsaturated fatty acids of FIG. 1 are added at a 1.5% actives to GLUCOPON® 625 CS SURFACTANT at about 40% actives, as measured by the Ross Miles test.
Figure 6:
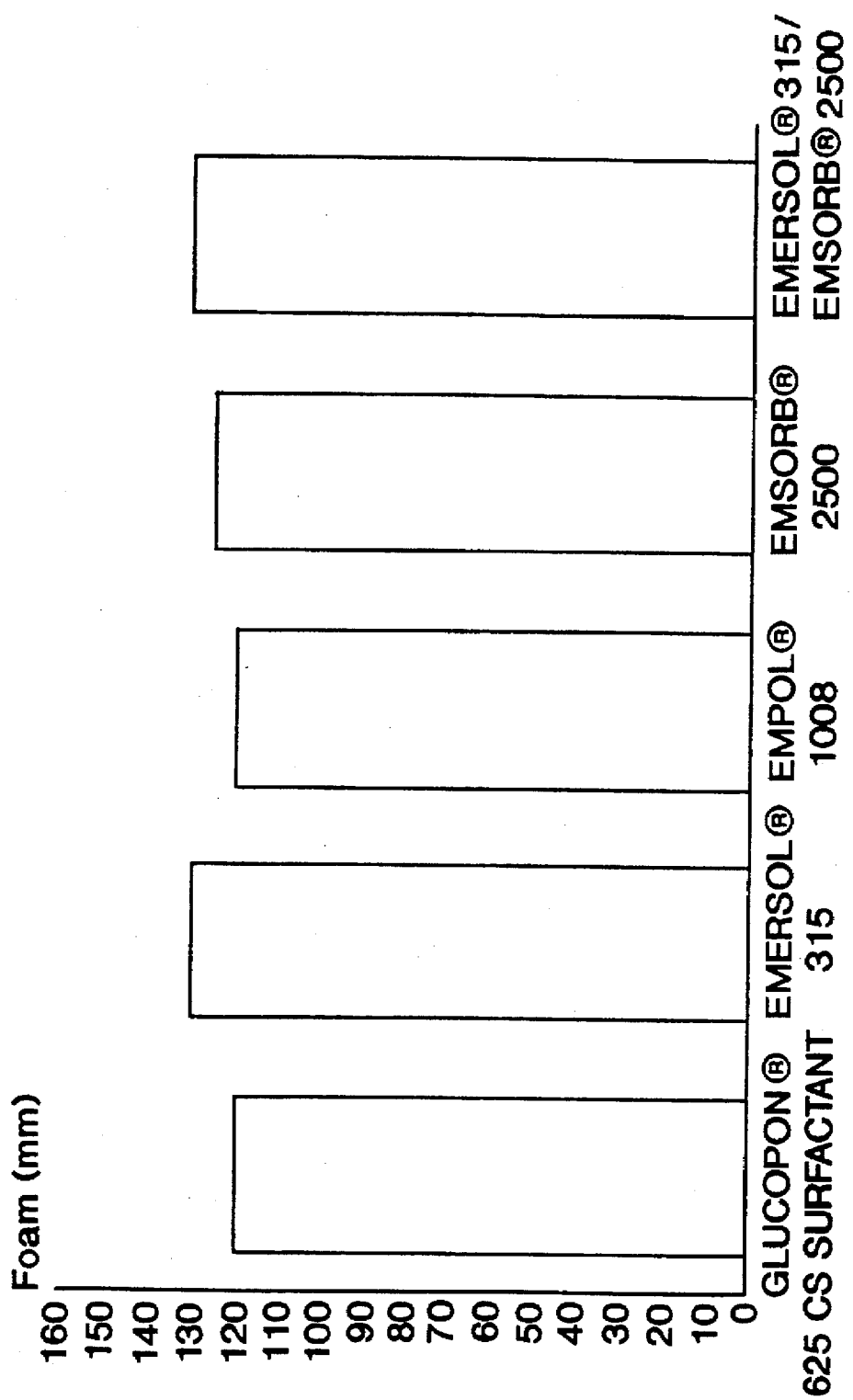
FIG. 6 is a bar graph illustrating the effect on the amount of foam formed at 72° F. in deionized water when the unsaturated fatty acids of FIG. 1 are added at a 1.5% actives to GLUCOPON® 625 CSUP SURFACTANT at about 40% actives, as measured by the Ross Miles test.
Figure 7:
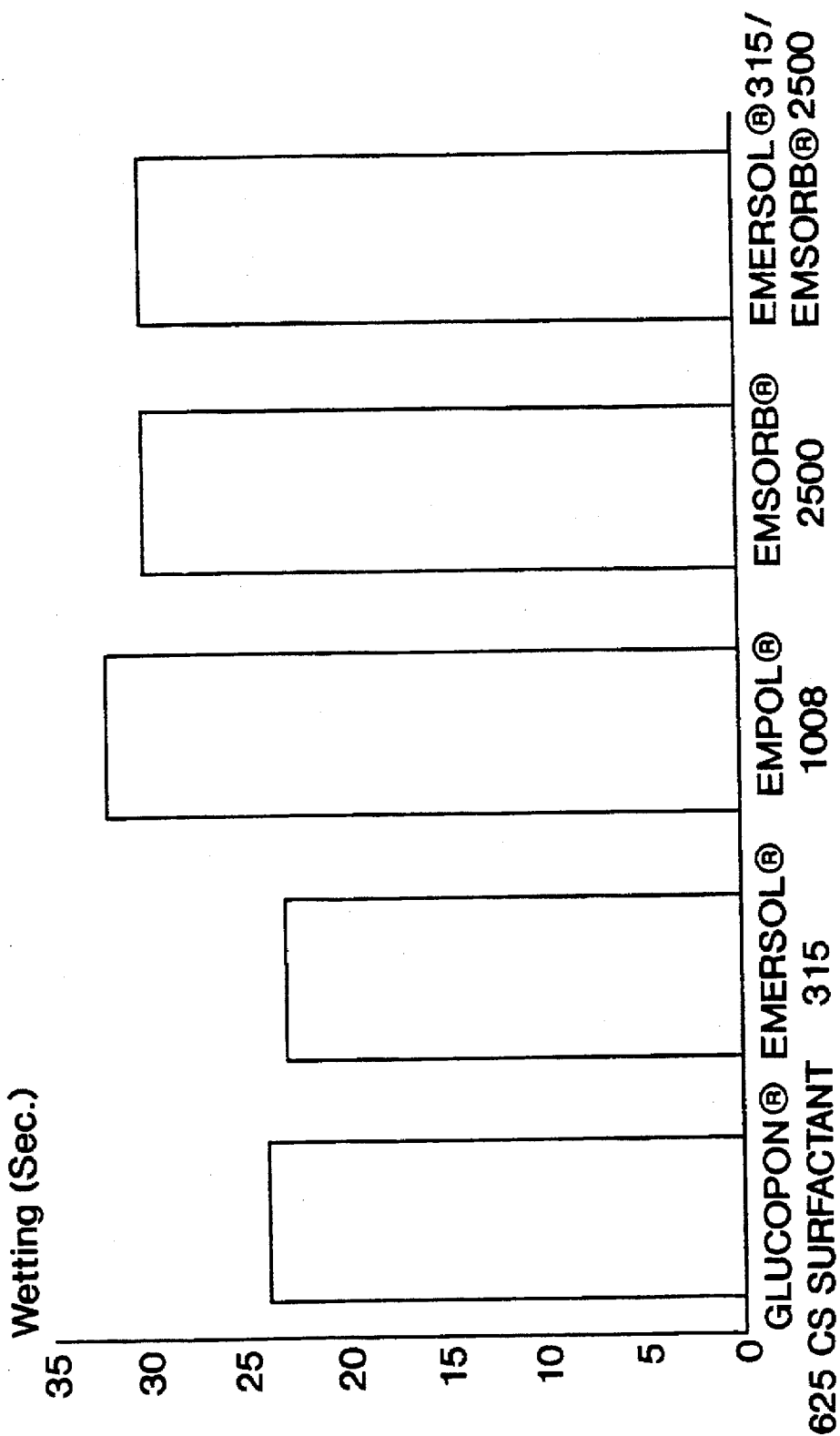
FIG. 7 is a bar graph illustrating the effect on wetting ability when the unsaturated fatty acids of FIG. 1 are added at a 1.5% actives to GLUCOPON® 625 CS SURFACTANT at about 40% actives at a temperature of about 72° F. in deionized water, as measured by the Draves Wetting test.
Figure 8:
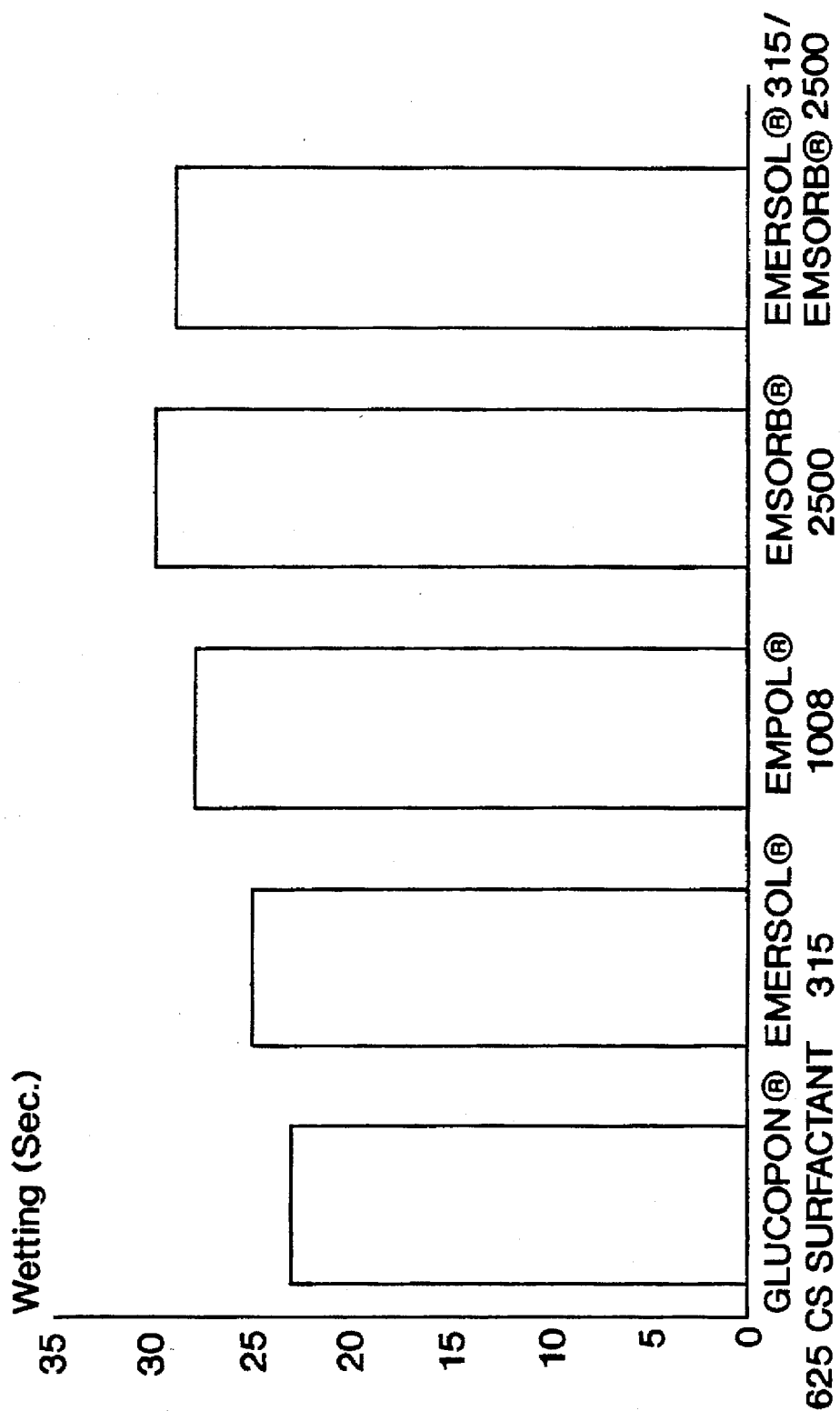
FIG. 8 is a bar graph illustrating the effect on wetting ability when the unsaturated fatty acids of FIG. 1 are added at a 1.5% actives to GLUCOPON® 625 CSUP SURFACTANT at about 40% actives at a temperature of about 72° F. in deionized water, as measured by the Draves Wetting test.

In Examples 1–4 and Comparative Example 1, 40 grams of 50% actives GLUCOPON® 625 CS SURFACTANT, an alkyl polyglycoside composition commercially available from Henkel Corp., Ambler, Pa. was charged into a beaker and heated to a temperature of about 40° C. Various additives were then added to the alkyl polyglycoside composition with thorough mixing. The compositions were then allowed to stand under ambient conditions for a predetermined number of days. The Examples were then evaluated for appearance to determine whether the formation of crystals was visible to the human eye. The Examples were then tested to determine their viscosities, foaming, wetting, and critical micelle concentration, the results of which can be found in FIGS. 1–8.

TABLE I

| No. | EMERSOL® 315 (K) | EMERSOL® 315 (Na) | EMPOL® 1008 | EMSORB® 2500 | APPEARANCE |
|---|---|---|---|---|---|
| 1 | 1.5 | — | — | — | clear |
| 2 | — | 1.5 | — | — | clear |
| 3 | — | — | 1.5 | — | clear |
| 4 | — | — | — | 1.5 | clear |
| C1 | — | — | — | — | hazy |

*(all components are represented in grams)

EMERSOL® 315 (K) is the potassium salt of linolic acid, commerciallly available from Henkel Corp., Emery Division, at 1.5% actives.

EMERSOL® 315 (Na) is the sodium salt of linolic acid, commercially available from Henkel Corp., Emery Division, at 1.5% actives.

EMPOL® 1008 is the potassium salt of dimmer acid, commercially available from Henkel Corp., Emery Division, at 1.5% actives.

EMSORB® 2500 is sorbitan mono oleate, commercially available from Henkel Corp., Emery Division, at 1.5% actives.

Examples 5–8 and Comparative Example 2 listed in Table II were prepared as per above using 80 grams of 40% actives GLUCOPON® 625 csup, an alkyl polyglycoside composition also commercially available from Henkel Corp. The Examples were then evaluated and tested, as per above.

TABLE II

| No. | EMERSOL® 315 (K) | EMERSOL® 315 (Na) | EMPOL® 1008 | EMSORB® 2500 | APPEARANCE |
|---|---|---|---|---|---|
| 5 | 1.5 | — | — | — | clear |
| 6 | — | 1.5 | — | — | clear |
| 7 | — | — | 1.5 | — | clear |
| 8 | — | — | — | 1.5 | clear |
| C2 | — | — | — | — | hazy |

*(all components are represented in grams)

As can be seen from the results in Tables I and II, as well as FIGS. 1–8, the addition of one of the disclosed additives such as an unsaturated fatty acid having a terminal anionic group thereon significantly inhibits or delays the formation of crystals in alkyl polyglycosides of formula I, without imparing its physical properties.

Thus enhancement of an alkyl polyglycoside's aesthetic appearance is desired, i.e., the inhibition of crystallization during storage at ambient conditions, the disclosed additive is preferably added in a weight ratio of alkyl polyglycoside to additive of about 25:1.

Tactile Improvement

Composition A 336.0 grams of PLANTAREN®-2000 (an alkyl polyglycoside commercially available from Henkel Corp., Emery division, was heated to 50° C., after which 26.9 grams of EMPOL® 1008 was added. The pH of the solution was adjusted to 7.2 with 11.6 grams of 25% NaOH solution. 18.7 grams of water was then added to the solution to adjust the solids to about 50%. The solution was then cooled to 25° C. The final product was clear yellow in appearance having a pH of 7.2 and a Brookfield viscosity of about 2,950 cps.

The following shampoo formulations were prepared in order to determine the tactile properties imparted by an alkyl polyglycoside composition of the present invention versus that of a control group.

Example 9

| COMPONENT | % by weight |
|---|---|
| STANDAPOL® ES-2 | 15.0 |
| STANDAMID® SD | 3.0 |
| Composition A | 15.0 |
| thickener | 0.5 |
| Citric acid soln., pH to 6.5 | 2.0 |
| water | 64.5 |
| | 100.0 |

STANDAPOL® ES-2 is ammonium laureth sulfate having a degree of ethoxylation of about 2, available from Henkel Corp., Emery Division.

STANDAMID® SD is cocamide DEA, available from Henkel Corp., Emery Division.

Comparison Example 3

| COMPONENT | % by weight |
|---|---|
| STANDAPOL® ES-2 | 15.0 |
| STANDAMID® SD | 3.0 |
| PLANTAREN® -2000 | 15.0 |
| thickener | 0.5 |
| Citric acid soln., pH to 6.5 | 2.0 |

| COMPONENT | % by weight |
| --- | --- |
| water | 64.5 |
| | 100.0 |

Test Procedure

Example 9 and Comparison Example 3 were used to wash human hair and then evaluated for the feel they imparted on the hair after washing. The results showed that those individuals using the alkyl polyglycoside composition of the present invention found their hair to be soft and supple after washing. Conversely, those washing with Comparison Example 3 found that their hair felt very dry and tacky immediately following the washing. Thus, it can be seen that by incorporating the alkyl polyglycoside composition of the present invention into personal care products, the resultant tactile properties are significantly enhanced.

It should be noted, however, that in a process for cleansing human hair and/or skin, the amount of additive will vary, depending on the particular type of cleansing formulation being employed. Typical hair shampoos contain the following components: $C_{8-22}$ alkyl sulfates and their salts which may be ethoxylated with from 1–50 moles of (EO), cocoamides their salts and derivatives thereof, along with citric acid, its salts and derivatives. Thus, the amount of additive to be added will to a certain extent depend on the additional components being employed, other than alkyl polyglycoside. However, where the components include: (a) a first alkyl polyglycoside in combination with an additive selected from the group consisting of $C_6$–$C_{10}$ alkyl sulfates, unsaturated aliphatic carboxylic acids including hydroxy-substituted derivatives thereof or their salts, unsaturated aliphatic sorbitan esters, $C_8$–$C_{36}$ branched aliphatic di-carboxylic acids, $C_6$–$C_{54}$ branched aliphatic tri-carboxylic acids, alkyl sulfosuccinates, a second alkyl polyglycoside wherein the alkyl group has from 4 to 10 carbon atoms, alkyl alkoxylates, alkyl and aryl phosphate esters, branched aliphatic carboxylic acids, unsaturated alcohols, Guerbet alcohols, alkoxylated C 6 to C 18 alkyl polyglycosides, alkoxylated penterythritol, alkoxylated penterythritol esters, alkyl and aryl sulfonates, alkyl sulfonates, alkenyl sulfonates, alkyl amino carboxylates or imino dicarboxylates, betaines, carboxylated imidazoline derivatives, carboxylate surfactants, and mixtures thereof; (b) alkyl sulfates and their salts; (c) fatty acid amides, the percent actives ratio of components (a)+(b):(c) will typically fall in the range of about 1:6 to about 1:4, and preferably about 1:1. The same holds true for body cleansers. The preferred additive for use in body cleanser formulations is a dicarboxylic acid having from about 8 to about 36 carbon atoms.

It will be recognized by those skilled in the art that changes may be made to the above-described embodiments of the invention without departing from the broad inventive concepts thereof. It is understood, therefore, that this invention is not limited to the particular embodiments disclosed, but is intended to cover all modifications which are within the scope and spirit of the invention as defined by the appended claims.

The invention claimed is:

1. A process for enhancing the aesthetic and tactile properties of an alkyl polyglycoside comprising adding an effective amount of an additive selected from the group consisting of $C_6$–$C_{10}$ alkyl sulfates, unsaturated aliphatic carboxylic acids including hydroxy-substituted derivatives thereof or their salts, unsaturated aliphatic sorbitan esters, $C_8$–$C_{36}$ branched aliphatic di-carboxylic acids, $C_6$–$C_{54}$ branched aliphatic tri-carboxylic acids, alkyl sulfosuccinates, a short-chain alkyl polyglycoside wherein the alkyl group has from 4 to 10 carbon atoms, alkyl alkoxylates, alkyl and aryl phosphate esters, branched aliphatic carboxylic acids, unsaturated alcohols, Guerbet alcohols, alkoxylated C 6 to C 18 alkyl polyglycosides, alkoxylated penterythritol, alkoxylated penterythritol esters, alkyl and aryl sulfonates, alkyl sulfonates, alkenyl sulfonates, alkyl amino carboxylates or imino dicarboxylates, betaines, carboxylated imidazoline derivatives, carboxylate surfactants, and mixtures thereof, to a first alkyl polyglycoside of formula I:

$$RO(Z)_a \qquad (I)$$

wherein R is a monovalent organic radical having from about 8 to about 18 carbon atoms; Z is a saccharide residue having 5 or 6 carbon atoms; and a is a number having a value from about 1 to about 6.

2. The process of claim 1 wherein said first alkyl polyglycoside and additive are present in a weight ratio of from about 500:1 to about 15:1, respectively.

3. The process of claim 2 wherein said ratio is about 25:1.

4. The process of claim 1 wherein said additive is an unsaturated aliphatic carboxylic acid including its hydroxy-substituted derivative or its salt.

5. The process of claim 4 wherein said unsaturated aliphatic carboxylic acid is in a salt form.

6. The process of claim 5 wherein said salt of said unsaturated aliphatic carboxlic acid is selected from the group consisting of potassium salt of linoleic acid, a sodium salt of linoleic acid, potassium salt of lenolenic acid, sodium salt of lenolenic acid and mixtures thereof.

7. The process of claim 1 wherein the weight ratio of said first alkyl polygycoside to said additive is about 25:1.

8. The process of claim 1 wherein said additive is an alkyl or alkenyl sulfonate.

9. The process of claim 1 wherein said additive is an alkyl amino carboxylate or imino dicarboxylate.

10. The process of claim 1 wherein said additive is a $C_6$–$C_{10}$ alkyl sulfate.

11. The process of claim 1 wherein said additive is a $C_8$–$C_{36}$ branched aliphatic di-carboxylic acid.

12. The process of claim 1 wherein said additive a $C_6$–$C_{54}$ branched aliphatic tri-carboxylic acid.

13. The process of claim 1 wherein said additive is an unsaturated aliphatic sorbitan ester.

14. The process of claim 1 wherein said additive is an alkyl sulfosuccinate.

15. The process of claim 1 wherein said additive is a short-chain alkyl polyglycoside wherein the alkyl group has from 4 to 10 carbon atoms.

16. The process of claim 1 wherein said additive is an alkyl alkoxylate.

17. The process of claim 1 wherein said additive is an alkyl and aryl phosphate ester.

18. The process of claim 1 wherein said additive is a branched aliphatic carboxylic acid.

19. The process of claim 1 wherein said additive is an unsaturated alcohol.

20. The process of claim 1 wherein said additive is a Guerbet alcohol.

21. The process of claim 1 wherein said additive is an alkoxylated $C_{8-18}$ alkyl polyglycoside.

22. The process of claim 1 wherein said additive is an alkoxylated penterythritol.

23. The process of claim 1 wherein said additive is an alkoxylated penterythritol ester.

24. The process of claim 1 wherein said additive is an alkyl and aryl sulfonate.

25. The process of claim 1 wherein said additive is a betaine.

26. The process of claim 1 wherein said additive is a carboxylated immidazoline derivative.

27. The process of claim 1 wherein said additive is a carboxylate surfactant.

28. The process of claim 1 wherein said first alkyl polyglycoside is an aqueous solution having a percent actives in the range from about 5 to about 80%.

29. The process of claim 28 wherein said percent actives is about 40%.

* * * * *